United States Patent
Falco et al.

(10) Patent No.: US 12,064,648 B2
(45) Date of Patent: Aug. 20, 2024

(54) CARDIAC ABLATION USING AN MR LINAC

(71) Applicant: Elekta LTD., Montreal (CA)

(72) Inventors: Tony Falco, La Prairie (CA); Martin Emile Lachaine, Montreal (CA)

(73) Assignee: Elekta LTD., Montreal (CA)

( * ) Notice: Subject to any disclaimer, the term of this patent is extended or adjusted under 35 U.S.C. 154(b) by 858 days.

(21) Appl. No.: 16/949,018

(22) Filed: Oct. 9, 2020

(65) Prior Publication Data
US 2021/0121715 A1     Apr. 29, 2021

Related U.S. Application Data

(60) Provisional application No. 62/927,327, filed on Oct. 29, 2019.

(51) Int. Cl.
*A61N 5/10* (2006.01)
*G06T 7/00* (2017.01)
(Continued)

(52) U.S. Cl.
CPC ......... *A61N 5/1039* (2013.01); *A61N 5/1045* (2013.01); *A61N 5/1049* (2013.01);
(Continued)

(58) Field of Classification Search
CPC .. A61N 5/1039; A61N 5/1045; A61N 5/1049; A61N 5/1067; A61N 5/107;
(Continued)

(56) References Cited

U.S. PATENT DOCUMENTS

| | | | |
|---|---|---|---|
| 10,765,336 B2 * | 9/2020 | Trayanova | G16H 50/50 |
| 2005/0245810 A1 * | 11/2005 | Khamene | G01R 33/56 |
| | | | 600/410 |

(Continued)

FOREIGN PATENT DOCUMENTS

| | | |
|---|---|---|
| AU | 2016201333 | 3/2016 |
| CN | 114728166 | 7/2022 |

(Continued)

OTHER PUBLICATIONS

"International Application Serial No. PCT CA2020 051357, International Search Report dated Dec. 8, 2020", 4 pgs.

(Continued)

*Primary Examiner* — Mark R Gaworecki
(74) *Attorney, Agent, or Firm* — Schwegman Lundberg & Woessner, P.A.

(57) ABSTRACT

Systems and methods are provided for performing operations comprising: generating a radiotherapy treatment plan for treating an ablation volume comprising a myocardial scar based on a first image of a patient that is generated using contrast-enhanced magnetic resonance (MR) imaging information; identifying, based on the first image of the patient, the ablation volume comprising the myocardial scar in a second image of the patient that is generated using MR imaging information without contrast; adjusting the radiotherapy treatment plan based on the ablation volume identified in the second image of the patient; acquiring a cine image of the patient during delivery of a radiotherapy treatment fraction by a radiotherapy treatment device based on the adjusted radiotherapy treatment plan; and comparing the cine image to the second image of the patient to control delivery of a radiotherapy beam by the radiotherapy treatment device.

31 Claims, 3 Drawing Sheets

(51) Int. Cl.
  *G06T 11/00* (2006.01)
  *G16H 20/40* (2018.01)
  *G16H 30/40* (2018.01)

(52) U.S. Cl.
  CPC ......... *A61N 5/1067* (2013.01); *A61N 5/1071* (2013.01); *G06T 7/0012* (2013.01); *G06T 11/008* (2013.01); *G16H 20/40* (2018.01); *G16H 30/40* (2018.01); *A61N 2005/1055* (2013.01); *A61N 5/107* (2013.01); *G06T 2207/10088* (2013.01); *G06T 2207/30096* (2013.01); *G06T 2210/41* (2013.01)

(58) Field of Classification Search
  CPC .......... A61N 5/1071; A61N 2005/1055; G06T 7/0012; G06T 11/008; G06T 2207/10088; G06T 2207/3006; G06T 2210/41; G16H 20/40; G16H 30/40
  See application file for complete search history.

(56) References Cited

U.S. PATENT DOCUMENTS

| | | | |
|---|---|---|---|
| 2008/0171931 A1* | 7/2008 | Maschke | A61B 6/4458 606/41 |
| 2012/0165652 A1* | 6/2012 | Dempsey | A61N 5/1045 600/410 |
| 2013/0182929 A1* | 7/2013 | Oshinski | G06T 11/005 382/128 |
| 2016/0022375 A1* | 1/2016 | Blake | A61B 5/02 600/424 |
| 2017/0371001 A1 | 12/2017 | Dempsey | |
| 2018/0318606 A1* | 11/2018 | Robinson | A61B 8/5261 |

FOREIGN PATENT DOCUMENTS

| | | |
|---|---|---|
| EP | 3256215 | 12/2017 |
| EP | 3266381 | 1/2018 |
| WO | WO-2011146779 A1 | 1/2011 |
| WO | WO-2017223382 A1 | 12/2017 |
| WO | 2018160763 | 9/2018 |
| WO | 2019118640 | 6/2019 |
| WO | 2021081626 | 5/2021 |

OTHER PUBLICATIONS

"International Application Serial No. PCT CA2020 051357, Written Opinion dated Dec. 8, 2020", 5 pgs.

"International Application Serial No. PCT CA2020 051357, International Preliminary Report on Patentability dated May 3, 2022", 7 pgs.

"European Application Serial No. 20881264.4, Response to Communication pursuant to Rules 161 and 162 filed Nov. 4, 2022", 14 pgs.

"European Application Serial No. 20881264.4, Extended European Search Report dated Oct. 19, 2023", 5 pgs.

"European Application No. 20881264.4, Observation Filed By 3rd Party, Oct. 1, 2024", (Oct. 1, 2024), 3 pgs.

"European Application Serial No. 20881264.4, Response filed Mar. 13, 2024 to Extended European Search Report mailed Oct. 19, 2023", 11 pgs.

Chin, Stephen, et al., "Magnetic Resonance Guided Radiation Therapy A Review", Journal of Medical Imaging and Radiation Oncology, (Oct. 23, 2019), 16 pgs.

Fischer-Valuck, Benjamin W., et al., "Two and a Half Year Clinical Experience With the World's First Magnetic Resonance Image Guided Radiation Therapy System", Advances in Radiation Oncology vol. 2 Issue 3, (Sep. 2017), 9 pgs.

Fuchs, Friedrich, et al., "TrueFISP Technical Considerations and Cardiovascular Applications", European Journal of Radiology vol. 46 Issue 1, (Apr. 2003), 5 pgs.

Ipsen, S., et al., "Radiotherapy Beyond Cancer Target Localization in Real Time MRI and Treatment Planning for Cardiac Radiosurgery", The International Journal of Medical Physics Research and Practice, (Nov. 17, 2014), 17 pgs.

Ipsen, S., et al., "Towards Real Time MRI Guided 3D Localization of Deforming Targets for Non Invasive Cardiac Radiosurgery", Physics in Medicine and Biology, (Oct. 25, 2016), 19 pgs.

\* cited by examiner

CARDIAC ABLATION USING AN MR LINAC

CLAIM FOR PRIORITY

This present application claims the benefit of priority to U.S. Provisional Application No. 62/927,327, filed Oct. 29, 2019, which is herein incorporated by reference in its entirety.

TECHNICAL FIELD

Embodiments of the present disclosure relates generally to radiation therapy or radiotherapy. More specifically, this disclosure relates to systems and methods for performing cardiac ablation using radiotherapy.

BACKGROUND

There is a growing trend to develop cardiac ablation techniques to treat ventricular tachycardia (VT) non-invasively from identification of the ablation volume (AV) to the treatment itself. Stereotactic body radiotherapy (SBRT) is one technique that is being considered for this purpose. This technique utilizes precisely targeted radiation to a tumor while minimizing radiation to adjacent normal tissue. This targeting allows treatment of small- or moderate-sized tumors in either a single or limited number of dose fractions. SBRT has unique radiobiological characteristics, which can cause dramatic tumor response, leading to the associated term "ablative" radiotherapy.

External beam radiotherapy is used to treat cancers and other ailments in mammalian (e.g., human and animal) tissue. External beam radiotherapy employs a radiotherapy device that accelerates particles (photons, electrons, and/or ions) to irradiate a tumor in a patient. One such radiotherapy device is a Gamma Knife, which irradiates a patient with a large number of low-intensity gamma rays that converge with high intensity and high precision at a target (e.g., a tumor). Another form of radiotherapy is brachytherapy, where a radiation source is placed inside or next to the area requiring treatment. The direction and shape of the radiation beam is accurately controlled to ensure the tumor receives the prescribed radiation dose, and the radiation from the beam should minimize damage to the surrounding healthy tissue, often called the organ(s) at risk (OARs). Treatment planning can be used to control radiation beam parameters, and a radiotherapy device effectuates a treatment by delivering a spatially varying dose distribution to the patient.

To perform SBRT the AV needs to be identified and a treatment plan needs to be created. Identification of the AV may be performed using localization of the anatomical scar using single-photon emission computed tomography imaging (SPECT), magnetic resonance imaging (MRI), computed tomography imaging (CT) and/or echocardiograms, as well as identification of activity using echocardiographic imaging (ECGI). ECGI relies on inducing VT via the patient's implantable cardioverter defibrillator (ICD), imaging with an electrocardiam (ECG), and mapping the external information internally using localization of the ECG leads on CT data.

Although ECGI can precisely localize the critical electrical elements of VT, it is only useful as partial information for building the AV during the treatment planning step. It is not available in the treatment room and thus cannot assist in daily image guidance or management of respiratory motion. As such, additional treatment margins, are usually added to account for respiratory motion which potentially increase side-effects.

Overview

The present disclosure includes procedures to generate a radiotherapy treatment plan for treating an ablation volume.

In some embodiments, a radiotherapy treatment plan is generated for treating an ablation volume comprising a myocardial scar based on a first image of a patient that is generated using contrast-enhanced magnetic resonance (MR) imaging information. The ablation volume comprising the myocardial scar is identified, based on the first image of the patient, in a second image of the patient that is generated using MR imaging information without contrast. The radiotherapy treatment plan is adjusted based on the ablation volume identified in the second image of the patient. A cine image of the patient is acquired during delivery of a radiotherapy treatment fraction by a radiotherapy treatment device based on the adjusted radiotherapy treatment plan. The cine image is compared to the second image of the patient to control delivery of a radiotherapy beam by the radiotherapy treatment device.

In some implementations, the first image comprises a three-dimensional (3D) planning image that is generated by: acquiring the contrast-enhanced MR imaging information of the patient using a cardiovascular magnetic resonance imaging (CMR) device; identifying the myocardial scar in the 3D planning image; and contouring the myocardial scar to generate the ablation volume based on the 3D planning image, wherein the myocardial scar is visible in contrast enhanced MR images and is not visible in MR images acquired without contrast.

In some implementations, the 3D pre-treatment image is registered to the 3D planning image using a deformable registration technique.

In some implementations, the cine image is registered to the 3D pre-treatment image.

In some implementations, a detection is made that the ablation volume is outside a threshold based on comparing the cine image to the second image; and delivery of the radiotherapy beam is paused in response to detecting that the ablation volume is outside the threshold.

In some implementations, geometric or dosimetric criteria is computed from registration values obtained by registering the cine image and the second image; and multi-leaf collimator (MLC) leaves of the radiotherapy treatment device are adjusted based on the computed geometric or dosimetric criteria.

In some implementations, the contrast-enhanced magnetic resonance (MR) imaging information and the MR imaging information without contrast are acquired under breath hold.

In some implementations, a margin is added to the ablation volume to generate the radiotherapy treatment plan, wherein the margin does not include effects of respiratory motion.

In some implementations, the patient is treated by the radiotherapy treatment device under breath hold or free breathing.

In some implementations, comparing the cine image to the second image comprises comparing the cine image to the second image using image registration or segmentation.

In some implementations, the contrast-enhanced MR imaging information of the patient is acquired using a cardiovascular magnetic resonance imaging (CMR) device, and the MR imaging information of the patient without contrast is acquired using a magnetic resonance imaging (MR) device that is part of the radiotherapy treatment device separate from the CMR device. In such cases, a coordinate system is matched between the CMR device and the MR device; and the ablation volume comprising the myocardial scar in the second image of the patient is identified based on the matched coordinate system.

In some implementations, the contrast-enhanced MR imaging information of the patient is acquired using a cardiovascular magnetic resonance imaging (CMR) device, and the MR imaging information of the patient without contrast is acquired using a magnetic resonance imaging (MR) device that is part of the radiotherapy treatment device separate from the CMR device. In such cases, correspondence between pixels in images provided by the CMR device and pixels in images provided by the MR device is determined; and the ablation volume comprising the myocardial scar in the second image of the patient is identified based on the determined correspondence.

In some implementations, the ablation volume comprising the myocardial scar is mapped from the first image to the second image.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

DETAILED DESCRIPTION

Systems and methods consistent with the present disclosure are directed to performing non-invasive cardiac ablation on an MR-Linac radiotherapy treatment device. Specifically, the disclosed embodiments include systems and methods for performing non-invasive cardiac ablation (e.g., for creating a radiotherapy treatment plan ("treatment plan")) using an improved radiotherapy technique. The disclosed techniques can be used to control delivery of radiotherapy by a radiotherapy device in real-time or near real-time during treatment of a patient. According to the disclosed embodiments, the VT can be treated non-invasively with reduced margins relative to traditional techniques.

Typically, radiotherapy treatment plans are generated based on imaging information, such as MR images of a patient. Specifically, a collection of MR images is captured and used to create a 3D planning image of a region of interest. A target is identified within the region of interest and the radiotherapy treatment plan is then created to direct a radiotherapy beam towards the target. As such, being able to visualize the target within the 3D planning image is key to creating an appropriate radiotherapy treatment plan. Oftentimes, myocardial scars may not be visible in the MR images that are collected. This introduces a challenge in generating a radiotherapy treatment plan that targets the myocardial scars which makes typical approaches unsuitable and unpractical to apply to treat myocardial scars or other targets that may not be visible in the MR images.

According to some embodiments, a radiotherapy treatment plan is generated to treat a myocardial scar by capturing images using contrast-enhanced MR images in which the myocardial scar is visible and finding correspondence of the location of the myocardial scar in MR images captured without contrast. Specifically, after identifying and contouring the myocardial scar in the contrast-enhanced MR image, a radiotherapy treatment plan is generated. At a later point in time (e.g., just prior to delivering the radiotherapy treatment to the patient), an MR image of the patient is obtained without contrast and the location, position, pixels, or other identifying components of the myocardial scar, as determined from the contrast-enhanced MR images, are mapped to the location of the myocardial scar that is not visible or for which visibility is limited in MR images obtained without contrast. The MR images captured without contrast are then used to adjust and update the radiotherapy treatment plan that was generated based on the contrast-enhanced MR images. As referred to herein, a contrast-enhanced MR image is an MR image that is captured while or immediately after a contrast agent is injected into a patient.

In some embodiments, an MR image of the myocardial scar is acquired with the patient in treatment position. This may be acquired with contrast-enhanced cardiac magnetic resonance (CMR) imaging for enhanced visualization of the scar, on the MR-Linac (radiotherapy treatment device) itself, or in a separate planning session on a different MR scanner. In some cases, the CMR images are acquired using breath hold. For example, the user may be instructed to hold their breath for certain lengths of time, and CMR image information is only acquired during these breath-hold periods. A three-dimensional (3D) planning image is generated from this acquired CMR imaging information. The images (e.g., the 3D planning image) are processed automatically or manually to identify the myocardial scar. This myocardial scar is contoured on the 3D planning image to generate the AV. Other information may also be integrated to define the AV, such as ECGI, SPECT, or CT images. Margins may be added to the AV to account for other uncertainties, but do not need to include the effects of respiratory motion. In this way, the margins according to the disclosed techniques can be smaller than the margins applied in typical techniques (e.g., in typical SBRT techniques). A treatment plan is then generated to treat the AV, for example, in a single radiotherapy treatment fraction.

A second 3D 'pre-treatment' image, which does not necessarily require contrast, is acquired, such as using MR imaging without contrast. The MR imaging may be acquired using the MR-Linac or another MR scanner. The pre-treatment image may be generated using MR images captured by the same or by a different device than that used to capture the CMR imaging for the 3D planning image. This second 3D image may be acquired also under breath hold in which the patient is instructed to hold their breath for certain lengths of time while the image is acquired. This second 3D pre-treatment image, generated using the MR images without contrast, is registered to the 3D planning image, generated using CMR images with contrast, such as using a deformable registration algorithm. The previously generated AV is adapted to the second 3D pre-treatment image using the calculated registration. The treatment plan may be adjusted or fully re-calculated based on the second 3D pre-treatment image.

In some embodiments, the patient is treated either under breath-hold or free breathing. During treatment, two-dimensional (2D) cine images are acquired and are compared to the 3D pre-treatment image. For example, the 2D cine images are compared to the 3D pre-treatment image using registration and/or segmentation techniques. Radiotherapy treatment is adjusted based upon these registration calculations. For example, the radiotherapy treatment may be adjustment by pausing the beam if the AV moves outside a given threshold and/or by adjusting multi-leaf collimator (MLC) leaves based upon geometric or dosimetric criteria calculated from the registration values.

In this way, the disclosed techniques can be used to treat a patient for VT with reduced side-effects and without the typical margin increases that account for respiratory motion. In some cases, four-dimensional (4D) MR images can be used instead of, or in addition to, breath hold to provide the planning and/or pre-treatment images.

Figure 1:
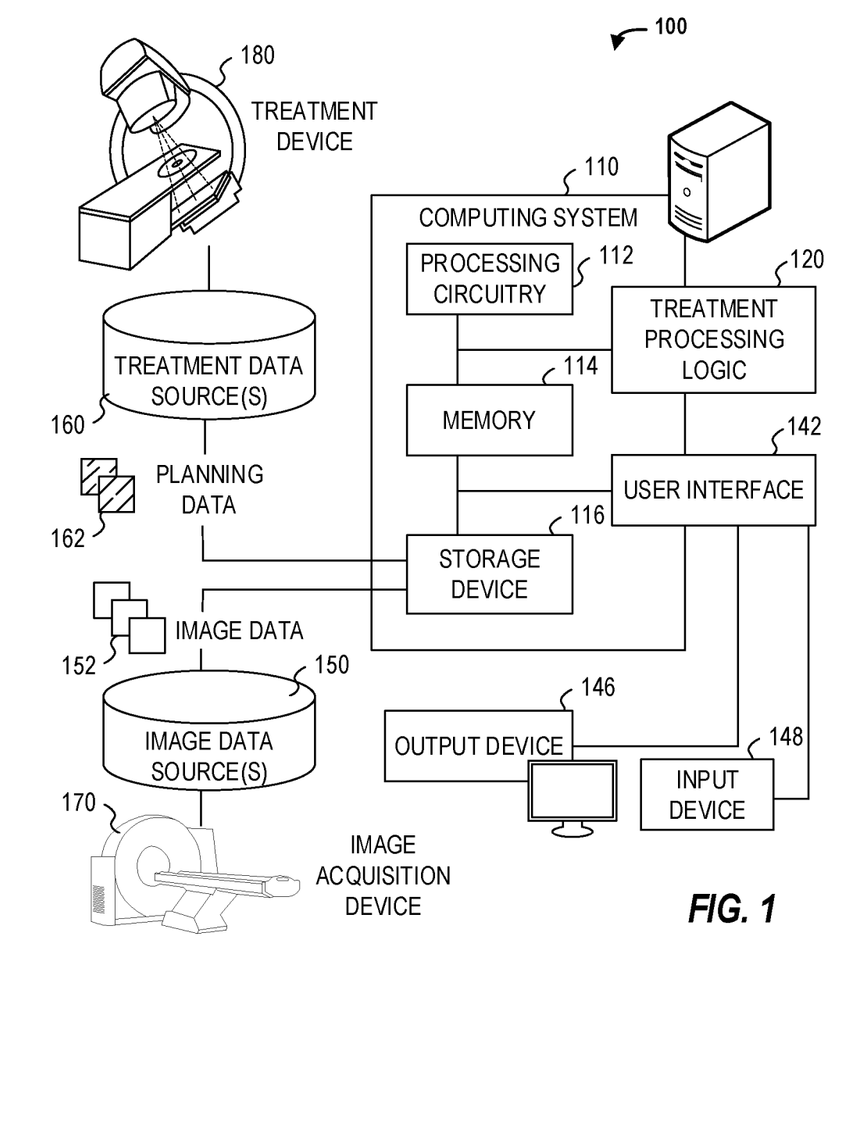
FIG. 1 illustrates an illustrative radiotherapy system adapted for performing treatment plan generation processing according to some examples.

FIG. 1 illustrates an exemplary radiotherapy system 100 adapted to perform radiotherapy plan processing operations using one or more of the approaches discussed herein. These radiotherapy plan processing operations are performed to enable the radiotherapy system 100 to provide radiation therapy to a patient based on specific aspects of captured medical imaging data and therapy dose calculations or radiotherapy machine configuration parameters.

The radiotherapy system 100 includes a radiotherapy processing computing system 110 which hosts treatment processing logic 120. The radiotherapy processing computing system 110 may be connected to a network (not shown), and such network may be connected to the Internet. For instance, a network can connect the radiotherapy processing computing system 110 with one or more medical information sources (e.g., a radiology information system (RIS), a medical record system (e.g., an electronic medical record (EMR)/electronic health record (EHR) system), an oncology information system (OIS)), one or more image data sources 150, an image acquisition device 170 (e.g., an imaging modality), a treatment device 180 (e.g., a radiation therapy device, also referred to herein as a radiotherapy device or radiotherapy treatment device), and a treatment data source 160. As an example, the radiotherapy processing computing system 110 can be configured to monitor current patient geometry to calculate dose delivery to a subject (e.g., from one or more 2D cine images) within a given fraction in real time and modify parameters of the radiotherapy treatment plan being executed by the radiotherapy device for subsequent doses delivered in the same fraction based on a comparison of the one or more 2D cine images to a 3D image of an AV.

The radiotherapy processing computing system 110 may include processing circuitry 112, memory 114, a storage device 116, and other hardware and software-operable features such as a user interface 142, a communication interface (not shown), and the like. The storage device 116 may store transitory or non-transitory computer-executable instructions, such as an operating system, radiation therapy treatment plans, software programs (e.g., image processing software, image or anatomical visualization software, artificial intelligence (AI) or ML implementations and algorithms such as provided by deep learning models, ML models, and neural networks, etc.), and any other computer-executable instructions to be executed by the processing circuitry 112.

In an example, the processing circuitry 112 may include a processing device, such as one or more general-purpose processing devices such as a microprocessor, a central processing unit (CPU), a graphics processing unit (GPU), an accelerated processing unit (APU), or the like. More particularly, the processing circuitry 112 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processing circuitry 112 may also be implemented by one or more special-purpose processing devices such as an application-specific integrated circuit (ASIC), a field programmable gate array (FPGA), a digital signal processor (DSP), a System on a Chip (SoC), or the like.

As would be appreciated by those skilled in the art, in some examples, the processing circuitry 112 may be a special-purpose processor, rather than a general-purpose processor. The processing circuitry 112 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. The processing circuitry 112 may also include graphical processing units such as a GPU from the GeForce®, Quadro®, Tesla® family manufactured by Nvidia™, GMA, Iris™ family manufactured by Intel™, or the Radeon™ family manufactured by AMD™. The processing circuitry 112 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one physical (circuitry based) or software based processor, for example, a multi-core design or a plurality of processors each having a multi-core design. The processing circuitry 112 can execute sequences of transitory or non-transitory computer program instructions, stored in memory 114, and accessed from the storage device 116, to perform various operations, processes, methods that will be explained in greater detail below. It should be understood that any component in system 100 may be implemented separately and operate as an independent device and may be coupled to any other component in system 100 to perform the techniques described in this disclosure.

The memory 114 may comprise read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a compact disc read-only memory (CD-ROM), a digital versatile disc (DVD) or other optical storage, a cassette tape, other magnetic storage device, or any other non-transitory medium that may be used to store information including images, training data, ML technique parameters, device adaptation functions, data, or transitory or non-transitory computer-executable instructions (e.g., stored in any format) capable of being accessed by the processing circuitry 112, or any other type of computer device. For instance, the computer program instructions can be accessed by the processing circuitry 112, read from the ROM, or any other suitable memory location, and loaded into the RAM for execution by the processing circuitry 112.

The storage device 116 may constitute a drive unit that includes a transitory or non-transitory machine-readable medium on which is stored one or more sets of transitory or non-transitory instructions and data structures (e.g., software) embodying or utilized by any one or more of the methodologies or functions described herein (including, in various examples, the treatment processing logic 120 and the user interface 142). The instructions may also reside, completely or at least partially, within the memory 114 and/or within the processing circuitry 112 during execution thereof by the radiotherapy processing computing system 110, with the memory 114 and the processing circuitry 112 also constituting transitory or non-transitory machine-readable media.

The memory 114 and the storage device 116 may constitute a non-transitory computer-readable medium. For example, the memory 114 and the storage device 116 may store or load transitory or non-transitory instructions for one or more software applications on the computer-readable medium. Software applications stored or loaded with the memory 114 and the storage device 116 may include, for example, an operating system for common computer systems as well as for software-controlled devices. The radiotherapy processing computing system 110 may also operate a variety of software programs comprising software code for implementing the treatment processing logic 120 and the user interface 142. Further, the memory 114 and the storage device 116 may store or load an entire software application, part of a software application, or code or data that is associated with a software application, which is executable by the processing circuitry 112. In a further example, the memory 114 and the storage device 116 may store, load, and manipulate one or more radiation therapy treatment plans, imaging data, segmentation data, treatment visualizations, histograms or measurements, AI model data (e.g., weights and parameters), training data, labels and mapping data, and the like. It is contemplated that software programs may be stored not only on the storage device 116 and the memory 114 but also on a removable computer medium, such as a hard drive, a computer disk, a CD-ROM, a DVD, a Blu-Ray DVD, USB flash drive, a SD card, a memory stick, or any other suitable medium; such software programs may also be communicated or received over a network.

Although not depicted, the radiotherapy processing computing system 110 may include a communication interface, network interface card, and communications circuitry. An example communication interface may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a IEEE 802.11/Wi-Fi adapter), a telecommunication adapter (e.g., to communicate with 3G, 4G/LTE, and 5G, networks and the like), and the like. Such a communication interface may include one or more digital and/or analog communication devices that permit a machine to communicate with other machines and devices, such as remotely located components, via a network. The network may provide the functionality of a local area network (LAN), a wireless network, a cloud computing environment (e.g., software as a service, platform as a service, infrastructure as a service, etc.), a client-server, a wide area network (WAN), and the like. For example, the network may be a LAN or a WAN that may include other systems (including additional image processing computing systems or image-based components associated with medical imaging or radiotherapy operations).

In an example, the radiotherapy processing computing system 110 may obtain image data 152 from the image data source 150 (e.g., MR images), for hosting on the storage device 116 and the memory 114. In yet another example, the software programs may substitute functions of the patient images such as signed distance functions or processed versions of the images that emphasize some aspect of the image information.

In an example, the radiotherapy processing computing system 110 may obtain or communicate image data 152 from or to image data source 150. In further examples, the treatment data source 160 receives or updates the planning data 162 as a result of radiotherapy device parameter adjustments generated by the treatment processing logic 120 (e.g., based on a comparison or registration of one or more 2D cine images to 3D images of an AV).

The processing circuitry 112 may be communicatively coupled to the memory 114 and the storage device 116, and the processing circuitry 112 may be configured to execute computer-executable instructions stored thereon from either the memory 114 or the storage device 116. The processing circuitry 112 may execute instructions to cause medical images from the image data 152 to be received or obtained in memory 114 and processed using the treatment processing logic 120.

In addition, the processing circuitry 112 may utilize software programs to generate intermediate data such as updated parameters to be used, for example, by a neural network model, or a machine learning model. Further, such software programs may utilize the treatment processing logic 120 to produce updated radiotherapy parameters to provide to the treatment data source 160 to modify a dose delivered to a target within a given fraction and/or for presentation on output device 146, using the techniques further discussed herein. The processing circuitry 112 may subsequently then transmit the updated radiotherapy parameters via a communication interface and the network to the treatment device 180, where the updated parameters will be used to treat a patient with radiation via the treatment device 180. Other outputs and uses of the software programs and the workflow 130 may occur with use of the radiotherapy processing computing system 110. Radiotherapy parameters may include MLC positions and settings, gantry angle, radiation dose amount (e.g., amount of monitor units (MU)), radiotherapy beam direction, radiation beam size, arc placement, beam on and off time duration, machine parameters, segments, gantry speed, MRI pulse sequence, any combination thereof, and so forth.

In the examples herein, the processing circuitry 112 may execute software programs that invoke the treatment processing logic 120 to implement functions of ML, deep learning, neural networks, generative machine learning model, a generative adversarial network, and other aspects of artificial intelligence for a device adaptation model (that specifies a device adaptation strategy and/or parameter adjustment amount) within a given fraction. For instance, the processing circuitry 112 may execute software programs that train, analyze, predict, evaluate, and generate a device adaptation model from a received treatment information of multiple patients.

In an example, the image data 152 may include one or more MRI image (e.g., 2D MRI, 3D MRI, 2D streaming MRI, 4D MRI, 4D volumetric MRI, 4D cine MRI, CMR images, contrast enhanced MR images, etc.), functional MRI images (e.g., fMRI, DCE-MRI, diffusion MRI), Computed Tomography (CT) images (e.g., 2D CT, 2D Cone beam CT, 3D CT, 3D CBCT, 4D CT, 4DCBCT), ECGI images, echocardiogram images, ultrasound images (e.g., 2D ultrasound, 3D ultrasound, 4D ultrasound), Positron Emission Tomography (PET) images, X-ray images, fluoroscopic images, radiotherapy portal images, Single-Photo Emission Computed Tomography (SPECT) images, computer-generated synthetic images (e.g., pseudo-CT images) and the like. Further, the image data 152 may also include or be associated with medical image processing data, for instance, training images, and ground truth images, contoured images, and dose images. In other examples, an equivalent representation of an anatomical area may be represented in non-image formats (e.g., coordinates, mappings, etc.).

In an example, the image data 152 may be received from the image acquisition device 170 and stored in one or more of the image data sources 150 (e.g., a Picture Archiving and Communication System (PACS), a Vendor Neutral Archive (VNA), a medical record or information system, a data warehouse, etc.). Accordingly, the image acquisition device 170 may comprise an MRI imaging device, a CT imaging device, a PET imaging device, an ultrasound imaging device, a fluoroscopic device, a SPECT imaging device, an echocardiogram imaging device, an ECGI imaging device, an integrated Linear Accelerator and MRI imaging device, CBCT imaging device, or other medical imaging devices for obtaining the medical images of the patient. The image data 152 may be received and stored in any type of data or any type of format (e.g., in a Digital Imaging and Communications in Medicine (DICOM) format) that the image acquisition device 170 and the radiotherapy processing computing system 110 may use to perform operations consistent with the disclosed embodiments. Further, in some examples, the models discussed herein may be trained to process the original image data format or a derivation thereof.

In an example, the image acquisition device 170 may be integrated with the treatment device 180 as a single apparatus (e.g., an MRI device combined with a linear accelerator, also referred to as an "MRI-Linac"). Such an MRI-Linac can be used, for example, to determine a location of a target in the patient, so as to direct linear or circular radiation therapy accurately according to the radiation therapy treatment plan to a predetermined target (e.g., an AV). For instance, a radiation therapy treatment plan may provide information about a particular radiation dose to be applied to each patient. The radiation therapy treatment plan may also include other radiotherapy information and radiotherapy device parameters, such as beam angles, dose-histogram-volume information, the number of radiation beams to be used during therapy, the dose per beam, and the like. In some embodiments, the MR-Linac device acquires the 2D cine images and compares the 2D cine images to the previously generated 3D pre-treatment image to adjust radiotherapy treatment.

In some embodiments, the image acquisition device 170 is configured to acquire a CMR image of the myocardial scar with a patient in treatment position. This CMR image may be acquired with contrast-enhanced CMR imaging for enhanced visualization of the scar, on the MR-Linac (radiotherapy treatment device) (e.g., treatment processing logic 120) itself, or in a separate planning session on a different MR scanner or imaging acquisition device 170. In some cases, the image acquisition device 170 acquires the images using breath hold where the user is instructed to hold their breath for certain lengths of time while the image information is only acquired during these breath-hold periods. In some implementations, the image acquisition device 170 generates a three-dimensional (3D) planning image from this acquired CMR imaging information. The image acquisition device 170 processes the 3D planning image automatically or manually to identify the myocardial scar. In some cases, the image acquisition device 170 uses machine learning techniques to identify portions of the 3D planning image in which the myocardial scar is present. This myocardial scar is contoured on the 3D planning image to generate the AV. In some cases, the image acquisition device 170 integrates or incorporates other information to define the AV, such as ECGI, SPECT, or CT images.

The treatment processing logic 120 receives the 3D planning image and adds margins to the AV to account for uncertainties. In some cases, the margins added by the treatment processing logic 120 do not include the effects of respiratory motion. In this way, the margins according to the disclosed techniques can be smaller than the margins applied in typical techniques (e.g., in typical SBRT techniques). The treatment processing logic 120 generates, automatically (e.g., using machine learning techniques) or manually, a treatment plan to treat the AV, for example, in a single radiotherapy treatment fraction.

In some embodiments, after the treatment plan to treat the AV is generated by the treatment processing logic 120, and just prior to the treatment session, the image acquisition device 170 generates a second 3D pre-treatment image which does not require contrast, such as using MR imaging information acquired without contrast. The image acquisition device 170 used to capture the CMR images for generating the 3D planning image may be the same or different from the image acquisition device 170 used to capture the MR imaging information without contrast for generating the 3D pre-treatment image. This second 3D pre-treatment image may be acquired also under breath hold in which the patient is instructed to hold their breath for certain lengths of time while the image is acquired.

The image acquisition device 170 registers this second 3D pre-treatment to the 3D planning image, such as using a deformable registration algorithm or machine learning techniques. In some cases, the image acquisition device 170 computes or determines a correspondence between CMR images captured with contrast and MR images captured without contrast by the same or different image acquisition device 170. For example, the contrast-enhanced MR imaging information of the patient is acquired using a cardiovascular magnetic resonance imaging (CMR) device and the MR imaging information of the patient without contrast is acquired using a magnetic resonance imaging (MR) device that is part of the radiotherapy treatment device separate from the CMR device. The image acquisition device 170 (or processing device coupled to the image acquisition device 170) matches the coordinate system between the CMR device and the MR device. By matching the coordinate system, the image acquisition device 170 is able to map a pixel in images acquired by the CMR device with those images acquired by the MR device. This way, a myocardial scar that may be apparent and visible in the CMR images and that is not visible in the MR images can nevertheless be identified in the MR images. Namely, pixels corresponding to the scar in the CMR images (e.g., pixels in the 3D planning image) are matched using the matched coordinate system to pixels in the MR images (e.g., pixels in the 3D pre-treatment image). In this way, a myocardial scar that is only visible in the CMR images can be treated by the radiotherapy treatment device that captures MR images without contrast. Specifically, the previously generated AV is adapted to the second 3D pre-treatment image using the calculated registration. The treatment plan may be adjusted or fully re-calculated based on the second 3D pre-treatment image.

During the treatment session for treating the AV, the treatment processing logic 120 communicates with the image acquisition device 170 to acquire 2D cine images. For example, the image acquisition device 170 may generate the 2D cine images that includes a sequence of 2D images that depict heart motion throughout the cardiac cycle in short clips. In some cases, the 2D cine images are obtained with ECG triggered segmented imaging. Segmented acquisition is the process of dividing the cardiac cycle into multiple segments (frames) to produce a series of images that can be displayed as a video clip (cine). The cardiac cycle begins with the R wave of the ECG, ends with the subsequent R wave and is divided into 10 to 20 segments, depending on the heart rate. Each image in the 2D cine images is composed of information gathered over several heart beats allowing for a video clip to be acquired with a breath hold of 10 to 20 seconds depending on the sequence. The final 2D cine images includes a sequence of individual frames. The 2D cine images may be obtained using MR imaging without contrast and may not visibly represent a myocardial scar.

The treatment processing logic 120 compares one or more portions or frames of the 2D cine images to the 3D pre-treatment image using registration and/or segmentation techniques. For example, the treatment processing logic 120 determines identifies a portion of the 2D cine images that correspond to pixels indicated in the pre-treatment image as corresponding to the myocardial scar. The treatment processing logic 120 determines whether the identified portion of the 2D cine images overlaps or is outside of the pixels indicated in the pre-treatment image as corresponding to the myocardial scar by more than a specified threshold. If so, the treatment processing logic 120 adjusts radiotherapy treatment based upon these registration calculations. For example, the radiotherapy treatment may be adjustment by pausing the beam if the AV moves outside a given threshold and/or by adjusting multi-leaf collimator (MLC) leaves based upon geometric or dosimetric criteria calculated from the registration values.

The threshold may be a value that is determined automatically or may be manually set by a user. The threshold value may be set based on a type of imaging device used to capture the CMR images and/or the MR images. For example, if the imaging device used to capture the CMR images for the planning image is different from the imaging device used to capture the MR images (without contrast) for the pre-treatment image, a first threshold may be computed and used to control the radiotherapy treatment in response to the AV moving outside the threshold. As another example, if the imaging device used to capture the CMR images for the planning image is the same as the imaging device used to capture the MR images (without contrast) for the pre-treatment image, a second threshold may be computed and used to control the radiotherapy treatment in response to the AV moving outside the threshold. The second threshold may be larger or smaller than the first threshold.

The radiotherapy processing computing system 110 may communicate with an external database through a network to send/receive a plurality of various types of data related to image processing and radiotherapy operations. For example, an external database may include machine data (including device constraints) that provides information associated with the treatment device 180, the image acquisition device 170, or other machines relevant to radiotherapy or medical procedures. Machine data information may include radiation beam size, arc placement, beam on and off time duration, machine parameters, segments, MLC configuration, gantry speed, MRI pulse sequence, and the like. The external database may be a storage device and may be equipped with appropriate database administration software programs. Further, such databases or data sources may include a plurality of devices or systems located either in a central or a distributed manner.

The radiotherapy processing computing system 110 can collect and obtain data, and communicate with other systems, via a network using one or more communication interfaces, which are communicatively coupled to the processing circuitry 112 and the memory 114. For instance, a communication interface may provide communication connections between the radiotherapy processing computing system 110 and radiotherapy system components (e.g., permitting the exchange of data with external devices). For instance, the communication interface may, in some examples, have appropriate interfacing circuitry from an output device 146 or an input device 148 to connect to the user interface 142, which may be a hardware keyboard, a keypad, or a touch screen through which a user may input information into the radiotherapy system.

As an example, the output device 146 may include a display device that outputs a representation of the user interface 142 and one or more aspects, visualizations, or representations of the medical images, the treatment plans, and statuses of training, generation, verification, or implementation of such plans. The output device 146 may include one or more display screens that display medical images, interface information, treatment planning parameters (e.g., contours, dosages, beam angles, labels, maps, etc.), treatment plans, a target, localizing a target and/or tracking a target, or any related information to the user. The input device 148 connected to the user interface 142 may be a keyboard, a keypad, a touch screen or any type of device using which a user may input information to the radiotherapy system 100. Alternatively, the output device 146, the input device 148, and features of the user interface 142 may be integrated into a single device such as a smartphone or tablet computer (e.g., Apple iPad®, Lenovo Thinkpad®, Samsung Galaxy®, etc.).

Furthermore, any and all components of the radiotherapy system 100 may be implemented as a virtual machine (e.g., via VMWare, Hyper-V, and the like virtualization platforms) or independent devices. For instance, a virtual machine can be software that functions as hardware. Therefore, a virtual machine can include at least one or more virtual processors, one or more virtual memories, and one or more virtual communication interfaces that together function as hardware. For example, the radiotherapy processing computing system 110, the image data sources 150, or like components, may be implemented as a virtual machine or within a cloud-based virtualization environment.

The image acquisition device 170 can be configured to acquire one or more images of the patient's anatomy for a region of interest (e.g., a target organ, a target tumor, an AV or both). Each image, typically a 2D image or slice, can include one or more parameters (e.g., a 2D slice thickness, an orientation, and a location, etc.). In an example, the image acquisition device 170 can acquire a 2D slice in any orientation. For example, an orientation of the 2D slice can include a sagittal orientation, a coronal orientation, or an axial orientation. The processing circuitry 112 can adjust one or more parameters, such as the thickness and/or orientation of the 2D slice, to include the target organ and/or target tumor. In an example, 2D slices can be determined from information such as a 3D CBCT or CT, or MRI volume. Such 2D slices can be acquired by the image acquisition device 170 in "near real-time" while a patient is undergoing radiation therapy treatment, for example, when using the treatment device 180 (with "near real-time" meaning acquiring the data without (or with minimal) lag between image acquisition and treatment, as known in the art).

In some embodiments, the treatment processing logic 120 controls delivery of radiotherapy to an AV of a patient in real-time or near real-time based on one or more 2D cine images captured by the image acquisition device 170. Specifically, the treatment processing logic 120 generates a radiotherapy treatment plan for treating an ablation volume based on a first image of a patient captured by the image acquisition device 170. In some cases, the first image is a 3D MR image that is acquired with contrast while the patient is under breath hold.

In an example, the first image is processed by the treatment processing logic 120 to identify a myocardial scar in the first image. In some implementations, the treatment processing logic 120 uses machine learning techniques and/or user input to identify the myocardial scar. The treatment processing logic 120 contours the myocardial scar to generate the ablation volume (AV). In some embodiments, the treatment processing logic 120 generates the radiotherapy treatment plan using machine learning (e.g., automated radiotherapy treatment plan generation) and/or based on input from a user. In some implementations, the treatment processing logic 120 adds a margin to the AV in the first image to account for uncertainties. The margin may not include the effects of respiratory motion.

After the radiotherapy treatment plan is generated for treating the AV, a second image is acquired. In some cases, the second image is a 3D MR image is acquired without contrast while the patient is under breath hold. The treatment processing logic 120 maps the AV from the 3D planning image generated using the CMR imaging information to the 3D MR image acquired without contrast. In one example, the treatment processing logic 120 registers the second image to the first image and adjusts the radiotherapy treatment plan based on the registration of the second image to the first image. In some case, the treatment processing logic 120 registers the second image to the first image using a deformable registration technique. Particularly, the treatment processing logic 120 identifies the AV in the second image and determines any differences between the position and/or size of the AV in the second image relative to the first image. Based on such differences, the treatment processing logic 120 updates and/or recalculates the radiotherapy treatment plan for treating the AV.

In some embodiments, while the patient is undergoing radiotherapy in a single radiotherapy treatment fraction (e.g., under breath hold or free breathing), the treatment processing logic 120 obtains one or more 2D cine images and updates or modifies parameters of the radiotherapy treatment plan based on the 2D cine images. Specifically, the treatment processing logic 120 compares a given 2D cine image (e.g., a location and/or size of the AV in the 2D cine image) to the AV in the second image. The treatment processing logic 120 determines differences in location and/or size of the AV based on this comparison and adjusts one or more parameters of the radiotherapy treatment plan. For example, the treatment processing logic 120 may determines that the ablation volume is outside a threshold based on the registered 2D cine image and the second image. In response, the treatment processing logic 120 pauses delivery of a radiotherapy beam. As another example, the treatment processing logic 120 computes geometric or dosimetric criteria from registration values obtained by registering the 2D cine image and the second image. The treatment processing logic 120 adjusts multi-leaf collimator (MLC) leaves of the radiotherapy treatment device based on the computed geometric or dosimetric criteria.

Figure 2:
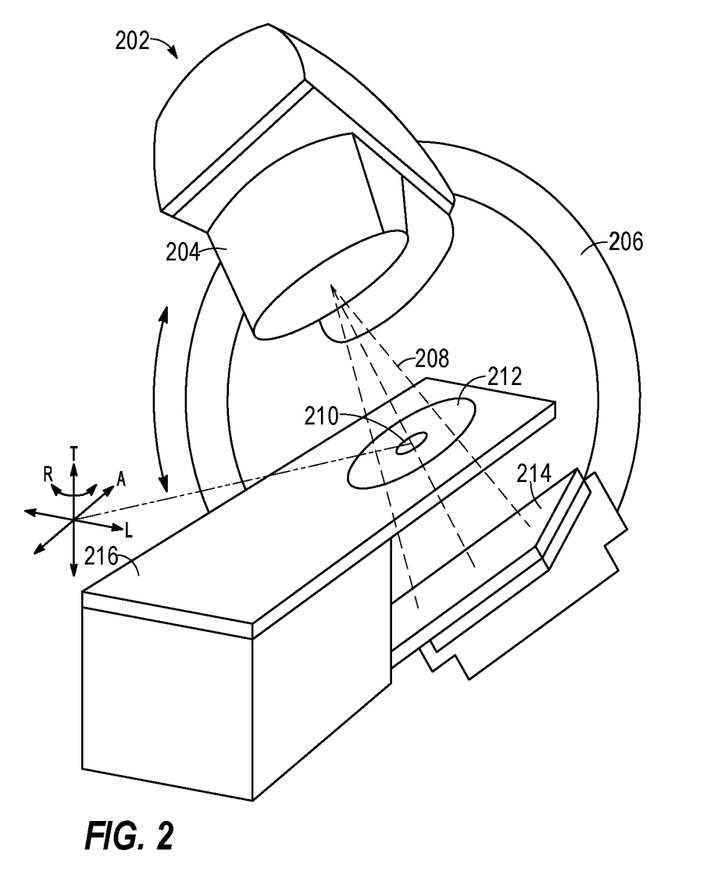
FIG. 2 illustrates an illustrative radiotherapy device according to some examples of the disclosure.

FIG. 2 illustrates an exemplary image-guided radiation therapy device 202 that includes a radiation source, such as an X-ray source or a linear accelerator, a couch 216, an imaging detector 214, and a radiation therapy output 204. The radiation therapy device 202 may be configured to emit a radiation therapy beam 208 to provide therapy to a patient. The radiation therapy output 204 can include one or more attenuators or collimators, such as a multi-leaf collimator (MLC).

As an example, a patient can be positioned in a region 212, supported by the treatment couch 216, to receive a radiation therapy dose according to a radiation therapy treatment plan. The radiation therapy output 204 can be mounted or attached to a gantry 206 or other mechanical support. One or more chassis motors (not shown) may rotate the gantry 206 and the radiation therapy output 204 around couch 216 when the couch 216 is inserted into the treatment area. In an example, gantry 206 may be continuously rotatable around couch 216 when the couch 216 is inserted into the treatment area. In another example, gantry 206 may rotate to a predetermined position when the couch 216 is inserted into the treatment area. For example, the gantry 206 can be configured to rotate the therapy output 204 around an axis ("A"). Both the couch 216 and the radiation therapy output 204 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 216 movements or rotations in order to properly position the patient in or out of the radiation therapy beam 208 according to a radiation therapy treatment plan. Both the couch 216 and the gantry 206 are independently moveable from one another in multiple degrees of freedom, which allows the patient to be positioned such that the radiation therapy beam 208 can precisely target the tumor.

The coordinate system (including axes A, T, and L) can have an origin located at an isocenter 210. The isocenter 210 can be defined as a location where the central axis of the radiation therapy beam 208 intersects the origin of a coordinate axis, such as to deliver a prescribed radiation dose to a location on or within a patient. Alternatively, the isocenter 210 can be defined as a location where the central axis of the radiation therapy beam 208 intersects the patient for various rotational positions of the radiation therapy output 204 as positioned by the gantry 206 around the axis A.

Gantry 206 may also have an attached imaging detector 214. The imaging detector 214 is preferably located opposite to the radiation source (output 204), and in an example, the imaging detector 214 can be located within a field of the radiation therapy beam 208. The imaging detector 214 can be mounted on the gantry 206, preferably opposite the radiation therapy output 204, such as to maintain alignment with the radiation therapy beam 208. The imaging detector 214 rotates about the rotational axis as the gantry 206 rotates. In an example, the imaging detector 214 can be a flat panel detector (e.g., a direct detector or a scintillator detector). In this manner, the imaging detector 214 can be used to monitor the therapy beam 208, or the imaging detector 214 can be used for imaging the patient's anatomy, such as portal imaging. The control circuitry of the radiation therapy device 202 may be integrated within the radiotherapy system 100 or remote from it.

In an illustrative example, one or more of the couch 216, the therapy output 204, or the gantry 206 can be automatically positioned, and the therapy output 204 can establish the radiation therapy beam 208 according to a specified dose for a particular therapy delivery instance. A sequence of therapy deliveries can be specified according to a radiation therapy treatment plan, such as using one or more different orientations or locations of the gantry 206, couch 216, or therapy output 204. The therapy deliveries can occur sequentially, but can intersect in a desired therapy locus on or within the patient, such as at the isocenter 210. A prescribed cumulative dose of radiation therapy can thereby be delivered to the therapy locus while damage to tissue nearby the therapy locus can be reduced or avoided.

Thus, FIG. 2 specifically illustrates an example of a radiation therapy device 202 operable to provide radiotherapy treatment to a patient consistent with or according to a radiotherapy treatment plan and parameters of a device adjusted within a given fraction, with a configuration where a radiation therapy output can be rotated around a central axis (e.g., an axis "A"). Other radiation therapy output configurations can be used. For example, a radiation therapy output can be mounted to a robotic arm or manipulator having multiple degrees of freedom. In yet another example, the therapy output can be fixed, such as located in a region laterally separated from the patient, and a platform supporting the patient can be used to align a radiation therapy isocenter with a specified target locus within the patient. In another example, a radiation therapy device can be a combination of a linear accelerator and an image acquisition device. In some examples, the image acquisition device may be an MRI, an X-ray, a CT, a CBCT, a spiral CT, a PET, a SPECT, an optical tomography, a fluorescence imaging, ultrasound imaging, or radiotherapy portal imaging device, etc., as would be recognized by one of ordinary skill in the art.

Figure 3:
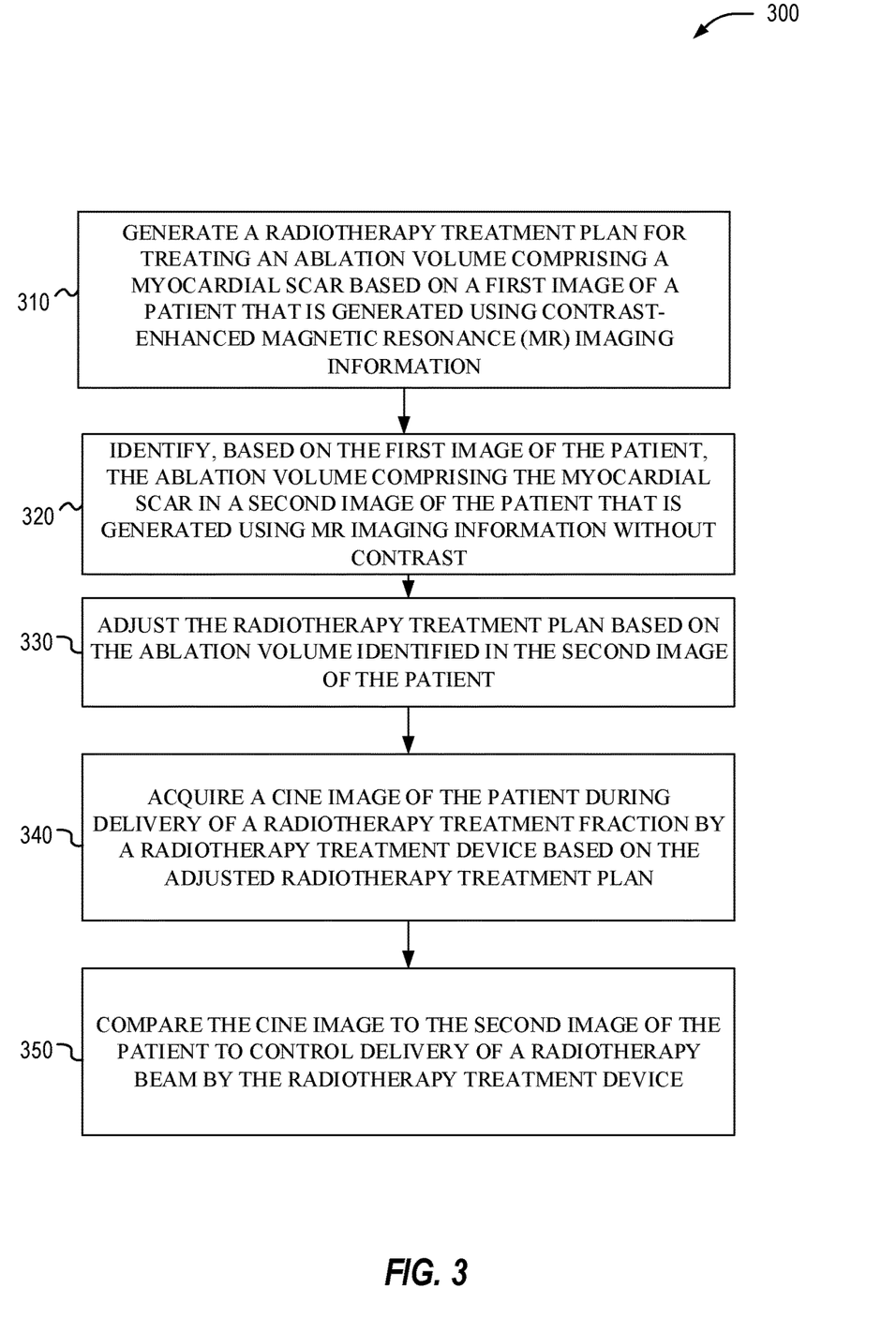
FIG. 3 illustrates an example flowchart of a process for performing non-invasive cardiac ablation according to some examples of the disclosure.

FIG. 3 is a flowchart of an illustrative process 300 of computing a radiotherapy dose distribution for a patient and can be implemented for example in a system shown in FIG. 1. The technologies described herein are consistent with different operating systems or hardware and can be applied in any variety of environments to take advantage of the described features. The process 300 may be embodied in computer-readable instructions for execution by one or more processors such that the operations of the process 300 may be performed in part or in whole by the functional components of the treatment processing logic 120; accordingly, the process 300 is described below by way of example with reference thereto. However, in other embodiments, at least some of the operations of the process 300 may be deployed on various other hardware configurations. The process 300 is therefore not intended to be limited to the treatment processing logic 120 and can be implemented in whole, or in part, by any other component. Some or all of the operations of process 300 can be in parallel, out of order, or entirely omitted.

At block 310, the treatment processing logic 120 generates a radiotherapy treatment plan for treating an ablation volume comprising a myocardial scar based on a first image of a patient that is generated using contrast-enhanced magnetic resonance (MR) imaging information.

At block 320, the treatment processing logic 120 identifies, based on the first image of the patient, the ablation volume comprising the myocardial scar in a second image of the patient that is generated using MR imaging information without contrast.

At block 330, the treatment processing logic 120 adjusts the radiotherapy treatment plan based on the ablation volume identified in the second image of the patient.

At block 340, the treatment processing logic 120 acquires a cine image of the patient during delivery of a radiotherapy treatment fraction by a radiotherapy treatment device based on the adjusted radiotherapy treatment plan.

At block 350, the treatment processing logic 120 compares the cine image to the second image of the patient to control delivery of a radiotherapy beam by the radiotherapy treatment device.

The technologies described herein have many advantages in the field of radiation therapy or radiotherapy. For example, computing a treatment plan dose distribution as described herein can significantly reduce computational time and required memory.

Additional Notes

As previously discussed, respective electronic computing systems or devices may implement one or more of the methods or functional operations as discussed herein. In one or more embodiments, the radiotherapy processing computing system may be configured, adapted, or used to control or operate the image-guided radiation therapy device, perform or implement the operations of the above processes, or perform any one or more of the other methodologies discussed. In various embodiments, such electronic computing systems or devices operates as a standalone device or may be connected (e.g., networked) to other machines. For instance, such computing systems or devices may operate in the capacity of a server or a client machine in server-client network environment, or as a peer machine in a peer-to-peer (or distributed) network environment. Features of computing systems or devices may be embodied by a personal computer (PC), a tablet PC, a Personal Digital Assistant (PDA), a cellular telephone, a web appliance, or any machine capable of executing instructions (sequential or otherwise) that specify actions to be taken by that machine.

As also indicated above, the functionality discussed above may be implemented by instructions, logic, or other information storage on a machine readable medium. While the machine-readable medium may have been described in various examples with reference to be a single medium, the term "machine-readable medium" may include a single medium or multiple media (e.g., a centralized or distributed database, and/or associated caches and servers) that store the one or more transitory or non-transitory instructions or data structures. The term "machine-readable medium" shall also be taken to include any tangible medium that is capable of storing, encoding or carrying transitory or non-transitory instructions for execution by the machine and that cause the machine to perform any one or more of the methodologies of the present disclosure, or that is capable of storing, encoding or carrying data structures utilized by or associated with such instructions.

The above detailed description includes references to the accompanying drawings, which form a part of the detailed description. The drawings show, by way of illustration but not by way of limitation, specific embodiments in which the disclosure can be practiced. These embodiments are also referred to herein as "examples." Such examples can include elements in addition to those shown or described. However, this disclosure also contemplates examples in which only those elements shown or described are provided. Moreover, the disclosure also contemplates examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the disclosure or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that after such a term (e.g., comprising, including, having) in a claim are still deemed to fall within the scope of that claim. Moreover, in the following claims, the terms "first," "second," and "third," etc., are used merely as labels, and are not intended to impose numerical requirements on their objects.

The present disclosure also relates to a computing system adapted, configured, or operated for performing the operations herein. This system may be specially constructed for the required purposes, or it may comprise a general purpose computer selectively activated or reconfigured by a computer program (e.g., instructions, code, etc.) stored in the computer. The order of execution or performance of the operations in embodiments of the disclosure illustrated and described herein is not essential, unless otherwise specified. That is, the operations may be performed in any order, unless otherwise specified, and embodiments of the disclosure may include additional or fewer operations than those disclosed herein. For example, it is contemplated that executing or performing a particular operation before, contemporaneously with, or after another operation is within the scope of aspects of the disclosure.

In view of the above, it will be seen that the several objects of the disclosure are achieved and other advantageous results attained. Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

The examples described herein may be implemented in a variety of embodiments. For example, one embodiment includes a computing device including processing hardware (e.g., a processor or other processing circuitry) and memory hardware (e.g., a storage device or volatile memory) including instructions embodied thereon, such that the instructions, which when executed by the processing hardware, cause the computing device to implement, perform, or coordinate the electronic operations for these techniques and system configurations. Another embodiment discussed herein includes a computer program product, such as may be embodied by a machine-readable medium or other storage device, which provides the transitory or non-transitory instructions to implement, perform, or coordinate the electronic operations for these techniques and system configurations. Another embodiment discussed herein includes a method operable on processing hardware of the computing device, to implement, perform, or coordinate the electronic operations for these techniques and system configurations.

In further embodiments, the logic, commands, or transitory or non-transitory instructions that implement aspects of the electronic operations described above, may be provided in a distributed or centralized computing system, including any number of form factors for the computing system such as desktop or notebook personal computers, mobile devices such as tablets, netbooks, and smartphones, client terminals and server-hosted machine instances, and the like. Another embodiment discussed herein includes the incorporation of the techniques discussed herein into other forms, including into other forms of programmed logic, hardware configurations, or specialized components or modules, including an apparatus with respective means to perform the functions of such techniques. The respective algorithms used to implement the functions of such techniques may include a sequence of some or all of the electronic operations described above, or other aspects depicted in the accompanying drawings and detailed description below.

The above description is intended to be illustrative, and not restrictive. For example, the above-described examples (or one or more aspects thereof) may be used in combination with each other. In addition, many modifications may be made to adapt a particular situation or material to the teachings of the disclosure without departing from its scope. While the dimensions, types of materials and example parameters, functions, and implementations described herein are intended to define the parameters of the disclosure, they are by no means limiting and are illustrative embodiments. Many other embodiments will be apparent to those of skill in the art upon reviewing the above description. The scope of the disclosure should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the disclosure should be determined with reference to the appended claims, along with the full scope of equivalents to which such claims are entitled.

What is claimed is:

1. A method comprising:
generating a radiotherapy treatment plan for treating an ablation volume comprising a myocardial scar based on a first image of a patient that is generated using contrast-enhanced magnetic resonance (MR) imaging information;
identifying, based on the first image of the patient, the ablation volume comprising the myocardial scar in a second image of the patient that is generated using MR imaging information without contrast;
adjusting the radiotherapy treatment plan based on the ablation volume identified in the second image of the patient;
acquiring a cine image of the patient during delivery of a radiotherapy treatment fraction by a radiotherapy treatment device based on the adjusted radiotherapy treatment plan; and
comparing the cine image to the second image of the patient to control delivery of a radiotherapy beam by the radiotherapy treatment device.

2. The method of claim 1, wherein the first image comprises a three-dimensional (3D) planning image that is generated by:
acquiring the contrast-enhanced MR imaging information of the patient using a cardiovascular magnetic resonance imaging (CMR) device;
identifying the myocardial scar in the 3D planning image; and
contouring the myocardial scar to generate the ablation volume based on the 3D planning image, wherein the myocardial scar is visible in contrast enhanced MR images and is not visible in MR images acquired without contrast.

3. The method of claim 2, wherein the second image comprises a 3D pre-treatment image, further comprising:
acquiring the MR imaging information without contrast of the patient using a magnetic resonance imaging (MR) device, wherein the MR device is part of the radiotherapy treatment device separate from the CMR device; and
registering the 3D pre-treatment image to the 3D planning image, wherein the radiotherapy treatment plan is adjusted or recalculated based on the registered pre-treatment image.

4. The method of claim 3, wherein the 3D pre-treatment image is registered to the 3D planning image using a deformable registration technique.

5. The method of claim 4, further comprising registering the cine image to the 3D pre-treatment image.

6. The method of claim 5, further comprising:
computing geometric or dosimetric criteria from registration values obtained by registering the cine image and the second image; and
adjusting multi-leaf collimator (MLC) leaves of the radiotherapy treatment device based on at least one of the computed geometric or dosimetric criteria.

7. The method of claim 1, further comprising:
detecting that the ablation volume is outside a threshold based on comparing the cine image to the second image; and
pausing delivery of the radiotherapy beam in response to detecting that the ablation volume is outside the threshold.

8. The method of claim 1, wherein the contrast-enhanced magnetic resonance (MR) imaging information and the MR imaging information without contrast are acquired under breath hold.

9. The method of claim 1, further comprising adding a margin to the ablation volume to generate the radiotherapy treatment plan, wherein the margin does not include effects of respiratory motion.

10. The method of claim 1, wherein the patient is treated by the radiotherapy treatment device under breath hold.

11. The method of claim 1, wherein comparing the cine image to the second image comprises comparing the cine image to the second image using at least one of image registration or segmentation.

12. The method of claim 1, wherein the contrast-enhanced MR imaging information of the patient is acquired using a cardiovascular magnetic resonance imaging (CMR) device, wherein the MR imaging information of the patient without contrast is acquired using a magnetic resonance imaging (MR) device that is part of the radiotherapy treatment device separate from the CMR device, further comprising:
matching a coordinate system between the CMR device and the MR device; and
identifying the ablation volume comprising the myocardial scar in the second image of the patient based on the matched coordinate system.

13. The method of claim 1, wherein the contrast-enhanced MR imaging information of the patient is acquired using a cardiovascular magnetic resonance imaging (CMR) device, wherein the MR imaging information of the patient without contrast is acquired using a magnetic resonance imaging (MR) device that is part of the radiotherapy treatment device separate from the CMR device, further comprising:
determining correspondence between pixels in images provided by the CMR device and pixels in images provided by the MR device; and
identifying the ablation volume comprising the myocardial scar in the second image of the patient based on the determined correspondence.

14. The method of claim 1, further comprising mapping the ablation volume comprising the myocardial scar from the first image to the second image.

15. A system comprising:
one or more processors configured to perform operations comprising:
generating a radiotherapy treatment plan for treating an ablation volume comprising a myocardial scar based on a first image of a patient that is generated using contrast-enhanced magnetic resonance (MR) imaging information;
identifying, based on the first image of the patient, the ablation volume comprising the myocardial scar in a second image of the patient that is generated using MR imaging information without contrast;
adjusting the radiotherapy treatment plan based on the ablation volume identified in the second image of the patient;
acquiring a cine image of the patient during delivery of a radiotherapy treatment fraction by a radiotherapy treatment device based on the adjusted radiotherapy treatment plan; and
comparing the cine image to the second image of the patient to control delivery of a radiotherapy beam by the radiotherapy treatment device.

16. The system of claim 15, wherein the first image comprises a three-dimensional (3D) planning image that is generated by:

acquiring the contrast-enhanced MR imaging information of the patient using a cardiovascular magnetic resonance imaging (CMR) device;
identifying the myocardial scar in the 3D planning image; and
contouring the myocardial scar to generate the ablation volume based on the 3D planning image, wherein the myocardial scar is visible in contrast enhanced MR images and is not visible in MR images acquired without contrast.

17. The system of claim 16, wherein the second image comprises a 3D pre-treatment image, further comprising operations for:
acquiring the MR imaging information without contrast of the patient using a magnetic resonance imaging (MR) device, wherein the MR device is part of the radiotherapy treatment device separate from the CMR device; and
registering the 3D pre-treatment image to the 3D planning image, wherein the radiotherapy treatment plan is at least one of adjusted or recalculated based on the registered pre-treatment image.

18. The system of claim 17, wherein the 3D pre-treatment image is registered to the 3D planning image using a deformable registration technique.

19. The system of claim 18, further comprising operations for registering the cine image to the 3D pre-treatment image.

20. The system of claim 19, further comprising operations for:
computing geometric or dosimetric criteria from registration values obtained by registering the cine image and the second image; and
adjusting multi-leaf collimator (MLC) leaves of the radiotherapy treatment device based on at least one of the computed geometric or dosimetric criteria.

21. The system of claim 15, further comprising operations for:
detecting that the ablation volume is outside a threshold based on comparing the cine image to the second image; and
pausing delivery of the radiotherapy beam in response to detecting that the ablation volume is outside the threshold.

22. The system of claim 15, wherein the contrast-enhanced magnetic resonance (MR) imaging information and the MR imaging information without contrast are acquired under breath hold.

23. The system of claim 15, further comprising operations for adding a margin to the ablation volume to generate the radiotherapy treatment plan, wherein the margin does not include effects of respiratory motion.

24. The system of claim 15, wherein the patient is treated by the radiotherapy treatment device under breath hold.

25. The system of claim 15, wherein comparing the cine image to the second image comprises comparing the cine image to the second image using at least one of image registration or segmentation.

26. The system of claim 15, wherein the contrast-enhanced MR imaging information of the patient is acquired using a cardiovascular magnetic resonance imaging (CMR) device, wherein the MR imaging information of the patient without contrast is acquired using a magnetic resonance imaging (MR) device that is part of the radiotherapy treatment device separate from the CMR device, further comprising operations for:
matching a coordinate system between the CMR device and the MR device; and
identifying the ablation volume comprising the myocardial scar in the second image of the patient based on the matched coordinate system.

27. The system of claim 15, wherein the contrast-enhanced MR imaging information of the patient is acquired using a cardiovascular magnetic resonance imaging (CMR) device, wherein the MR imaging information of the patient without contrast is acquired using a magnetic resonance imaging (MR) device that is part of the radiotherapy treatment device separate from the CMR device, further comprising operations for:
determining correspondence between pixels in images provided by the CMR device and pixels in images provided by the MR device; and
identifying the ablation volume comprising the myocardial scar in the second image of the patient based on the determined correspondence.

28. The system of claim 15, further comprising operations for mapping the ablation volume comprising the myocardial scar from the first image to the second image.

29. A non-transitory computer-readable medium comprising non-transitory computer-readable instructions that, when executed by one or more processors, configure the one or more processors to perform operations comprising:
one or more processors configured to perform operations comprising:
generating a radiotherapy treatment plan for treating an ablation volume comprising a myocardial scar based on a first image of a patient that is generated using contrast-enhanced magnetic resonance (MR) imaging information;
identifying, based on the first image of the patient, the ablation volume comprising the myocardial scar in a second image of the patient that is generated using MR imaging information without contrast;
adjusting the radiotherapy treatment plan based on the ablation volume identified in the second image of the patient;
acquiring a cine image of the patient during delivery of a radiotherapy treatment fraction by a radiotherapy treatment device based on the adjusted radiotherapy treatment plan; and
comparing the cine image to the second image of the patient to control delivery of a radiotherapy beam by the radiotherapy treatment device.

30. The non-transitory computer-readable medium of claim 29, wherein the first image comprises a three-dimensional (3D) planning image that is generated by:
acquiring the contrast-enhanced MR imaging information of the patient using a cardiovascular magnetic resonance imaging (CMR) device;
identifying the myocardial scar in the 3D planning image; and
contouring the myocardial scar to generate the ablation volume based on the 3D planning image, wherein the myocardial scar is visible in contrast enhanced MR images and is not visible in MR images acquired without contrast.

31. The non-transitory computer-readable medium of claim 30, wherein the second image comprises a 3D pre-treatment image, further comprising operations for:
acquiring the MR imaging information without contrast of the patient using a magnetic resonance imaging (MR) device, wherein the MR device is part of the radiotherapy treatment device separate from the CMR device; and registering the 3D pre-treatment image to the 3D planning image, wherein the radiotherapy treatment plan is adjusted or recalculated based on the registered pre-treatment image.

* * * * *